(12) United States Patent
Fleming

(10) Patent No.: US 9,649,221 B2
(45) Date of Patent: May 16, 2017

(54) THERAPY DEVICE FOR APPENDAGES

(71) Applicant: Jerome James Fleming, Hobart, IN (US)

(72) Inventor: Jerome James Fleming, Hobart, IN (US)

(*) Notice: Subject to any disclaimer, the term of this patent is extended or adjusted under 35 U.S.C. 154(b) by 262 days.

(21) Appl. No.: 14/067,161

(22) Filed: Oct. 30, 2013

(65) Prior Publication Data
US 2015/0057620 A1 Feb. 26, 2015

Related U.S. Application Data

(60) Provisional application No. 61/868,119, filed on Aug. 21, 2013.

(51) Int. Cl.
A61J 1/14 (2006.01)
A61M 35/00 (2006.01)
A61F 7/00 (2006.01)

(52) U.S. Cl.
CPC ........... A61F 7/0053 (2013.01); A61F 7/007 (2013.01); A61F 2007/0036 (2013.01)

(58) Field of Classification Search
CPC combination set(s) only.
See application file for complete search history.

(56) References Cited

U.S. PATENT DOCUMENTS

| 100,863 | A | * | 3/1870 | Corbett | A47J 27/10 126/377.1 |
| 1,534,618 | A | * | 4/1925 | Taylor | A61H 35/006 4/622 |
| 1,715,043 | A | * | 5/1929 | St John Oye | A61H 35/006 128/200.14 |
| 2,904,037 | A | * | 9/1959 | Cassidy | A61H 33/6089 392/458 |
| 3,055,357 | A | * | 9/1962 | Redka | A61H 35/006 601/15 |
| 3,283,756 | A | * | 11/1966 | Turley | A61H 35/006 15/104.92 |
| 3,649,971 | A | * | 3/1972 | Basa | A61H 33/06 4/527 |
| 3,757,806 | A | * | 9/1973 | Bhaskar | A61C 17/028 134/191 |
| 3,837,334 | A | * | 9/1974 | Johnson | A61H 35/006 601/19 |
| 3,845,759 | A | * | 11/1974 | Miklovic | A47K 3/10 4/541.3 |
| 3,918,987 | A | * | 11/1975 | Kopfer | A61B 90/80 134/113 |
| 3,965,495 | A | * | 6/1976 | McNair | A61H 35/006 4/622 |

(Continued)

Primary Examiner — Tatyana Zalukaeva
Assistant Examiner — Guy K Townsend
(74) Attorney, Agent, or Firm — Dunlap Bennett & Ludwig PLLC

(57) ABSTRACT

A housing for soaking a hand with arthritis, trauma, or skin conditions. The housing may include an outside container and an inside container. The outside container may house the components. There may be a channel between the inside container and the outside container. The present invention may include a heating element and an impeller within the channel. In certain embodiments, the heating element and impeller housing may be attached to the bottom of a lid that covers the housing.

4 Claims, 4 Drawing Sheets

(56) References Cited

U.S. PATENT DOCUMENTS

| | | | | |
|---|---|---|---|---|
| 4,057,053 A | * | 11/1977 | Kunz | A47K 3/10 601/158 |
| 4,196,479 A | * | 4/1980 | Geisler | A61H 33/10 4/524 |
| 4,217,892 A | * | 8/1980 | Brill | A61H 33/0087 4/509 |
| 4,338,944 A | * | 7/1982 | Arkans | A61F 7/10 607/104 |
| 4,497,313 A | * | 2/1985 | Kurosawa | A61H 35/006 601/156 |
| 4,620,529 A | * | 11/1986 | Kurosawa | A61H 35/006 601/157 |
| 4,817,651 A | * | 4/1989 | Crisp | A61B 90/80 134/102.1 |
| 4,880,415 A | * | 11/1989 | Urakami | A61F 7/0085 604/291 |
| 4,945,901 A | * | 8/1990 | Burcke, Jr. | A61H 23/0245 601/157 |
| 5,074,322 A | * | 12/1991 | Jaw | A47K 10/48 134/102.3 |
| 5,241,953 A | * | 9/1993 | Sykes | A61H 9/00 601/165 |
| 5,241,958 A | * | 9/1993 | Noeldner | A61H 35/00 4/541.4 |
| 5,476,489 A | * | 12/1995 | Koewler | A61F 7/10 607/104 |
| 5,806,335 A | * | 9/1998 | Herbert | A61F 7/10 607/114 |
| 5,921,250 A | * | 7/1999 | Rhea | A45D 29/007 132/73 |
| D442,284 S | * | 5/2001 | Ferber | A47K 3/022 D24/200 |
| D449,110 S | * | 10/2001 | Schmidt | A61H 23/00 D24/200 |
| D455,214 S | * | 4/2002 | Ferber | A47K 3/022 D24/204 |
| 6,438,768 B1 | * | 8/2002 | Yen | A47K 3/022 4/622 |
| 6,568,000 B1 | * | 5/2003 | Kaufman | A47K 3/022 4/541.5 |
| 6,602,212 B1 | * | 8/2003 | Ahn | A61H 33/6057 4/541.6 |
| 6,632,188 B2 | * | 10/2003 | Thomas | A61H 9/0078 601/152 |
| 6,725,471 B2 | * | 4/2004 | Ferber | A47K 3/022 4/541.5 |
| 6,805,678 B2 | * | 10/2004 | Cafaro | A61H 23/00 4/535 |
| D506,830 S | * | 6/2005 | Zimmermann | A47K 3/022 D24/204 |
| D531,732 S | * | 11/2006 | Bean | A47K 3/022 D24/213 |
| 7,150,720 B2 | * | 12/2006 | Adkins | A61H 9/0078 601/104 |
| 7,165,555 B2 | * | 1/2007 | Lee | A45D 29/00 132/73.5 |
| D537,949 S | * | 3/2007 | Lie | A47K 3/022 D24/213 |
| 7,426,757 B2 | * | 9/2008 | Lev | A61H 15/0078 220/761 |
| 8,216,291 B1 | * | 7/2012 | Leventhal | A61H 23/02 607/104 |
| D668,769 S | * | 10/2012 | Schmitz | A47K 3/022 D24/204 |
| 8,696,605 B2 | * | 4/2014 | Nichols | A61H 7/004 601/17 |
| 2005/0027218 A1 | * | 2/2005 | Filtvedt | A61F 7/00 601/152 |
| 2006/0207017 A1 | * | 9/2006 | Lev | A61H 33/027 4/622 |
| 2011/0098793 A1 | * | 4/2011 | Lowe | A61F 7/02 607/104 |
| 2011/0112450 A1 | * | 5/2011 | Null | A61F 13/041 602/3 |
| 2011/0307038 A1 | * | 12/2011 | Stiehr | A61F 7/0085 607/104 |
| 2011/0319972 A1 | * | 12/2011 | Skloss | A61F 7/0053 607/114 |
| 2013/0245729 A1 | * | 9/2013 | Edelman | A61F 7/10 607/104 |
| 2014/0212908 A1 | * | 7/2014 | Lelkes | A61K 49/0008 435/29 |
| 2015/0057620 A1 | * | 2/2015 | Fleming | A61F 7/0053 604/289 |
| 2015/0157490 A1 | * | 6/2015 | Wellborn | A61F 5/4408 604/345 |

* cited by examiner

THERAPY DEVICE FOR APPENDAGES

CROSS-REFERENCE TO RELATED APPLICATION

This application claims the benefit of priority of U.S. provisional application No. 61/868,119, filed Aug. 21, 2013, the contents of which are herein incorporated by reference.

BACKGROUND OF THE INVENTION

The present invention relates to a therapy device and, more particularly, to a container for soaking an appendage.

Skin trauma is a serious and altering physical injury caused by damage to the skin or multiple layers of epithelial tissues. This can be in the form of cuts, burns, sickness or other injury. Arthritis is a form of joint disorder that involves inflammation of one or more joints. For relief, generally users may mix Epsom salt with water in a bowl and place their appendage within the bowl.

As can be seen, there is a need for an improved device that relieves pain caused by arthritis and skin trauma.

SUMMARY OF THE INVENTION

In one aspect of the present invention, a therapeutic device comprises: a housing comprising an outside container and an inside container, wherein a channel is formed in between the outside container and the inside container, and wherein the inside container comprises at least one slot leading from the channel and into the inside container, and wherein the inside container is sized to fit a human appendage; and at least one actuated water circulator within the channel.

These and other features, aspects and advantages of the present invention will become better understood with reference to the following drawings, description and claims.

DETAILED DESCRIPTION OF THE INVENTION

Figure 1:
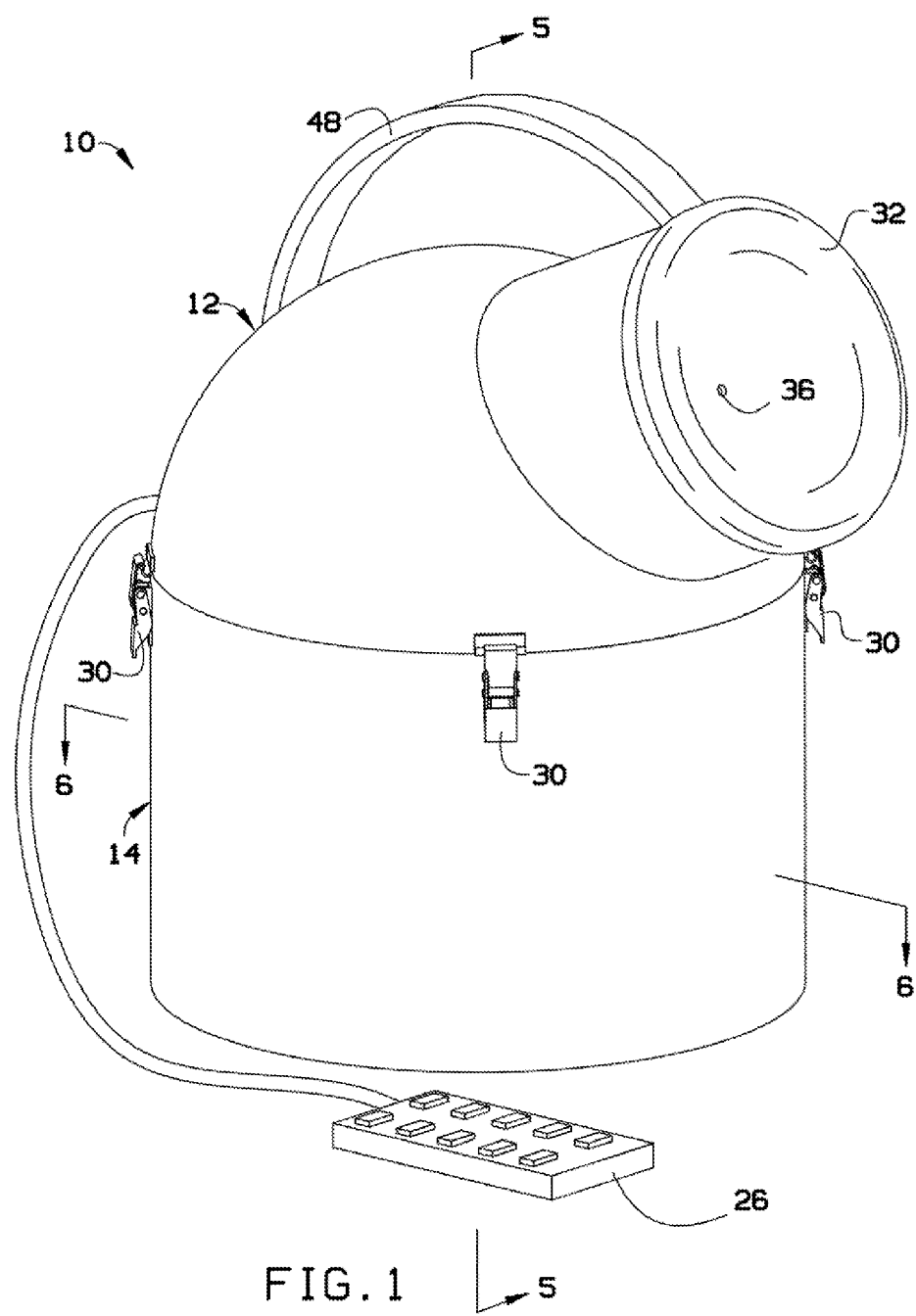
FIG. 1 is a perspective view of the present invention.
Figure 2:
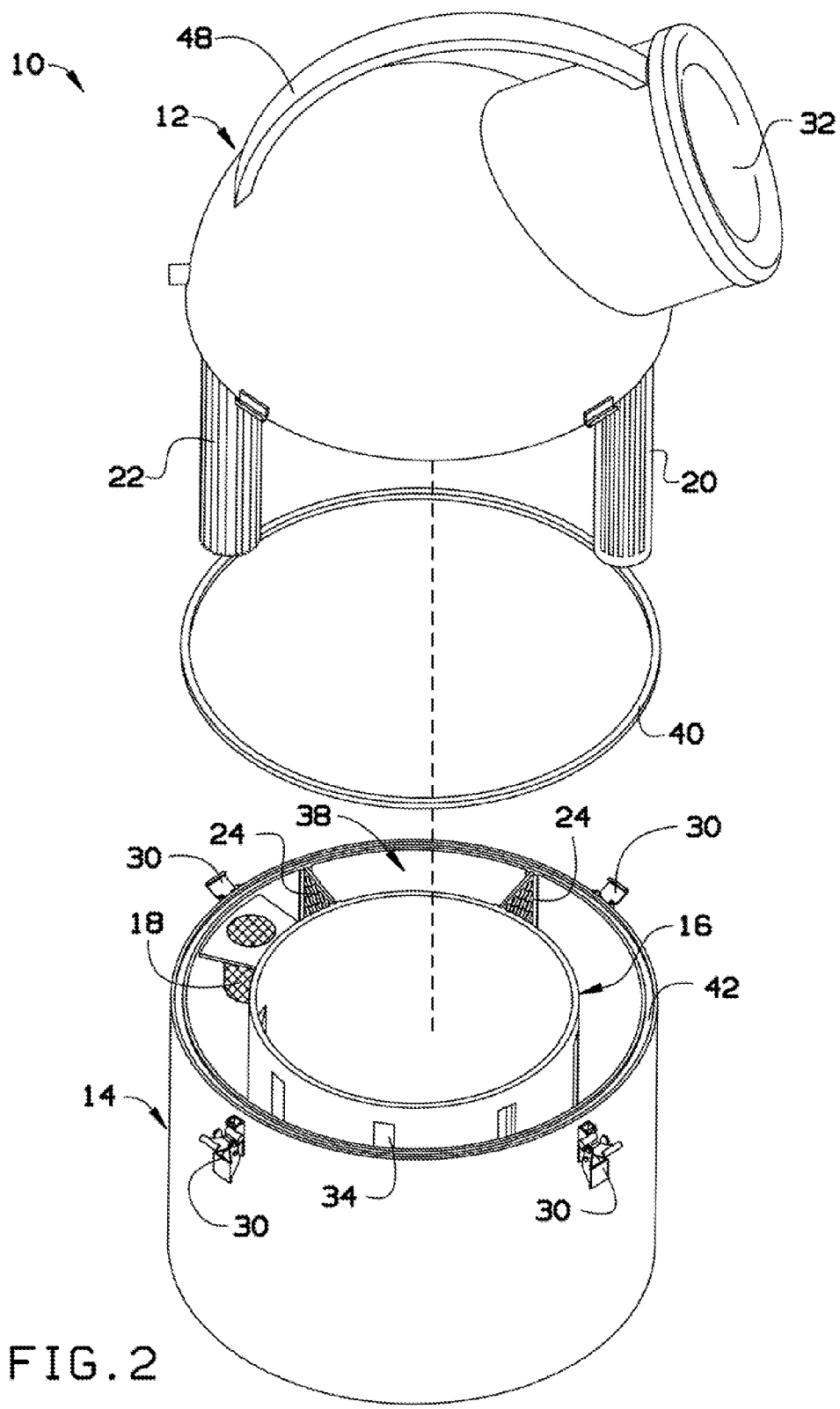
FIG. 2 is an exploded view of the present invention.
Figure 3:
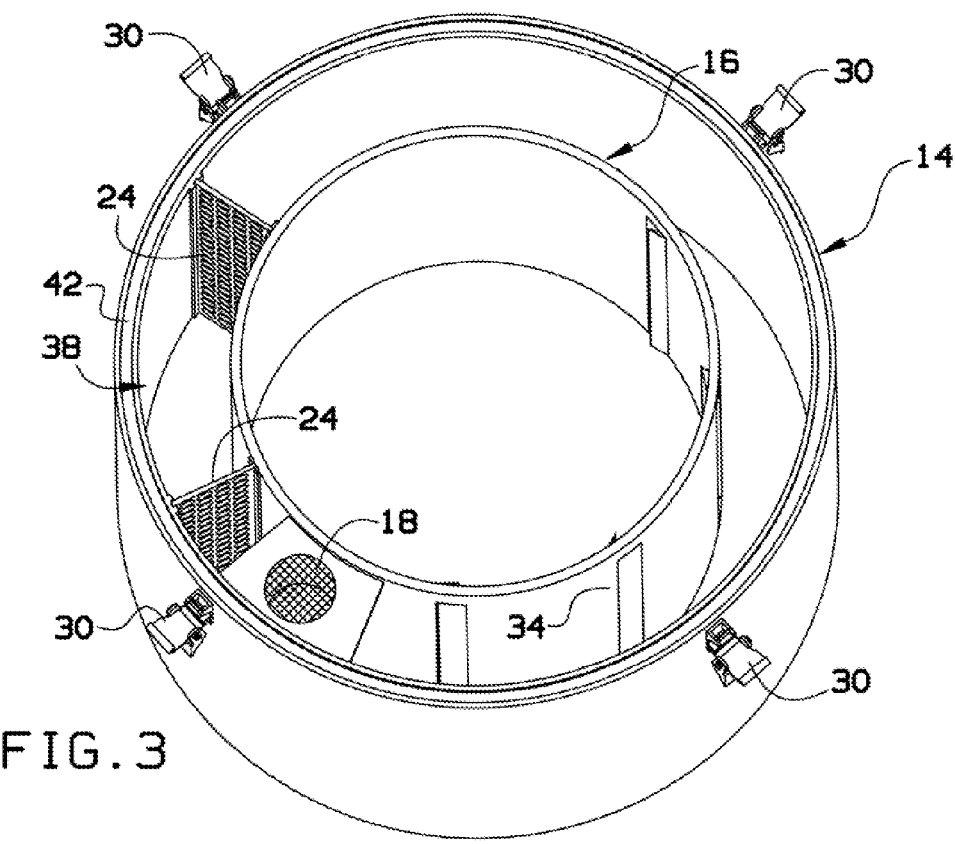
FIG. 3 is a top perspective view of the present invention showing the outside container and inner parts.
Figure 4:
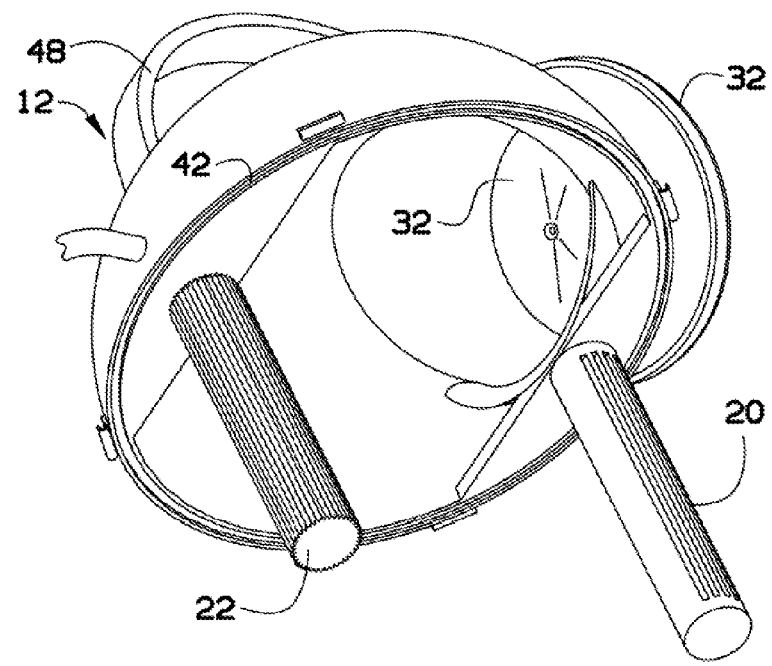
FIG. 4 is a bottom perspective view of the preset invention showing the top lid and associated inner parts.
Figure 5:
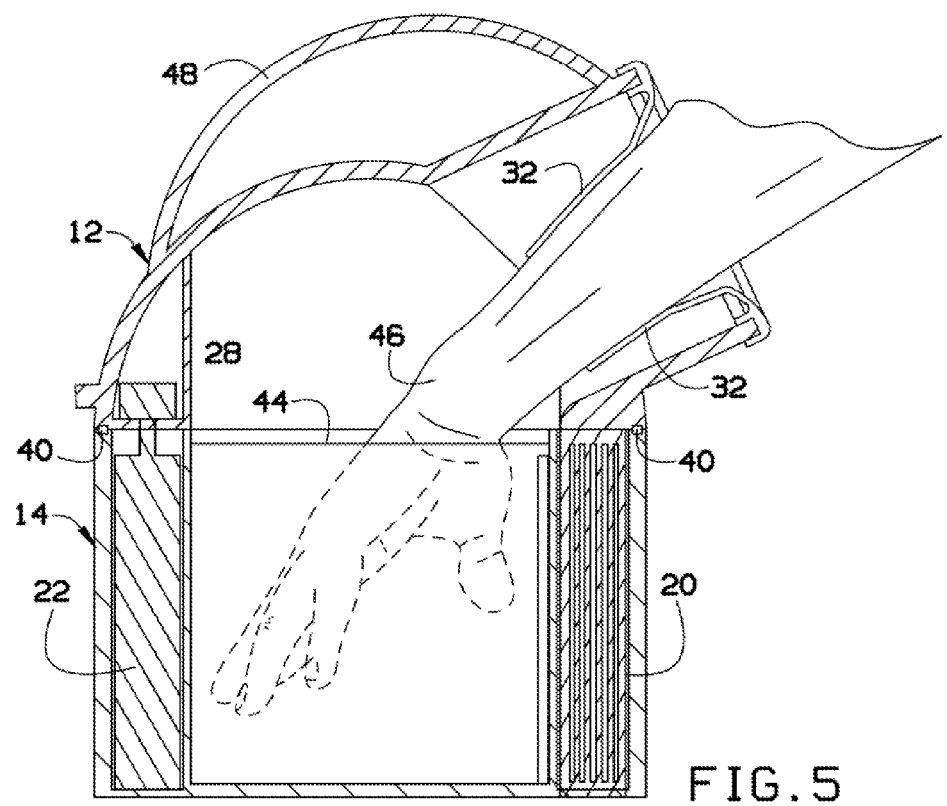
FIG. 5 is a section detail view of the present invention along line 5-5 in FIG. 1 demonstrated in use.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a housing for soaking a hand with arthritis, trauma, or skin conditions. The housing may include an outside container and an inside container. The outside container may house the components. There may be a channel between the inside container and the outside container. The present invention may include a heating element and an impeller within the channel. In certain embodiments, the heating element and impeller housing may be attached to the bottom of a lid that covers the housing.

Referring to FIGS. 1 through 6, the present invention may include a therapeutic housing 10. The housing 10 may include an outside container 14 and an inside container 16 within the outside container 14. A channel may be formed in between the inside container 16 and the outside container 14. The channel may be about 1 and ½ inches. The inside container 16 may include at least one slot 34, such as a plurality of slots 34. Therefore, water may flow from the channel and into the inside container 14. In certain embodiments, the inside container 16 may include three different sized slots 34 spaced at about 60 degrees to allow water to circulate in a gentle swirling motion around the hand 46 inside the inside container 16. There may be at least one actuated water circulator 22 within the channel, which may circulate the water from the channel and into the inside container 16. The inside container 16 may be sized to fit a human appendage such as a hand 46.

Figure 6:
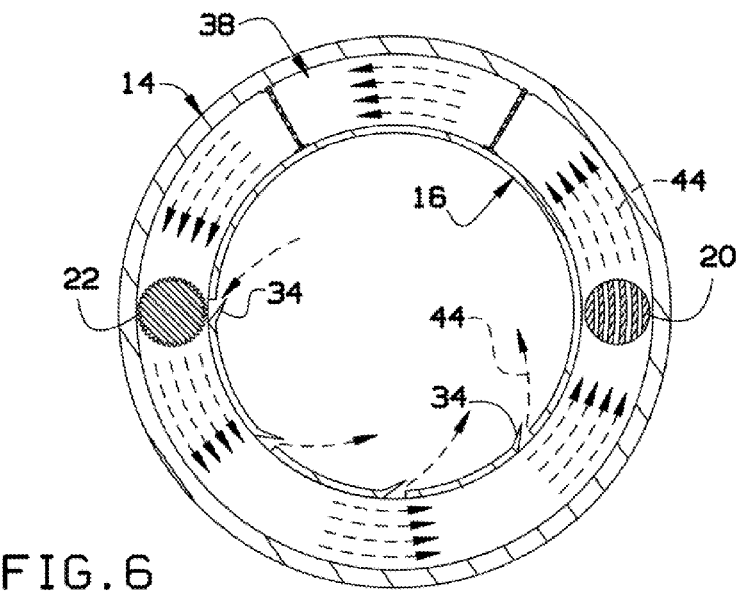
FIG. 6 is a section detail view of the present invention along line 6-6 in FIG. 1 demonstrated in use.

As mentioned above, the actuated water circulator 22 may circulate the water flow 44 within the housing 10. The actuated water circulator 22 may be a powered motor or a non-powered device actuated by a human. For example, the actuated water circular 22 may be a propeller or an impeller attached to a motor 28 to rotate the water within the housing 10. The water may flow 44 around the channel and into the inside container 16 through the plurality of slots 34. In certain embodiments, the plurality of slots 34 may include a first slot 34 and a second slot 34. The first slot 34 directs water from the channel into the inside container 16 and the second slot 34 directs water from the inside container 16 to the channel. As illustrated in FIG. 6, the water flows 44 from the channel into the inside container 16 through the first slot 34 and from the inside container 16 to the channel through the second slot 34.

In certain embodiments, the present invention may also include a heating element 20. The heating element 20 may be suspended within the channel. Therefore, the heating element 20 may heat up the water flowing 44 through the channel and provide a heated water swirl within the inside compartment 16. Alternatively, a user may poor hot water within the housing 10 without using the heating element 30; however, the temperature of the water would not be maintained.

In certain embodiments, the present invention may further include a top lid 12. The top lid 12 may include a top end and a bottom end. The bottom end is formed to fit over and cover the housing 10. In certain embodiments, the bottom end may be releasably attachable to the housing 10 by clips 30 or other securing devices. A gasket 40 which may fit within a gasket channel 42 at the top of the housing 10 may provide a tighter seal. An opening may be formed at the top end of the top lid 12.

In certain embodiments, a latex wrist seal 32 may cover the opening. The top of the lid 12 may have a raised top with a cylinder shape protruding out with the wrist seal 32 on the outside allowing the hand 46 to be inserted to the inside container 16 sealing around the wrist to contain any water splashing. The latex wrist seal 32 may include a latex wrist seal entrance 36. Therefore, a user may stick their hand within the entrance 36 through the latex wrist seal 32 and into the housing 10 with the rotating water flow 44. The lid 12 may further include a handle 48.

In certain embodiments, the heating element 20 and the actuated water circulator 22 may be attached to the bottom end of the lid 12. The heating element 20 and the actuated water circulator 22 may be attached to the outside rim of the lid 12 and may therefore be positioned so that when the lid 12 is attached to the housing 10, the actuated water circulator 22 and the heating element 20 may be suspended within the channel. The present invention may further include a control panel operatively attached to the water circulator 22 and the heating element 20. Therefore, a user may control the speed of the water flow and the temperature of the water.

The present invention may further include add-ons. For example, the present invention may include at least a first partition 24 and at least a second partition 24. The first and second partitions 24 may be dividers with apertures. The first and second partitions 24 may attach the outside container 14 to the inside container 16. The first and second partitions 24 may form a cavity 38 in between. Therefore a user may place ice, herbs, a tea bag or the like to further add therapeutic affects to the water. The present invention may include a strainer basket 18. The strainer basket 18 may contain herbs or Epsom salt. The channel may also house the strainer basket 18 allowing the water to circulate through the herbs, etc. releasing the healing properties to the water.

The following is a method of using the present invention. The user may decide what herbs work best for arthritis, trauma, or skin condition. Epsom salt or sea water may be used. The user may choose whether to use cool or heat therapy. Once this is done the user may fill the container with water, add the herbs in the strainer or cavity, add ice for cold therapy, place the lid on, close snap levers, plug in, sit down, insert hand, turn on and set to desired flow level, set the heat if using heat therapy, and relax and enjoy. Once completed, the byproduct of used herbs may be compost for house plants or gardens.

It should be understood, of course, that the foregoing relates to exemplary embodiments of the invention and that modifications may be made without departing from the spirit and scope of the invention as set forth in the following claims.

What is claimed is:

1. A therapeutic device for providing continuously heated fluid to a human appendage, the therapeutic device comprising:
   (a) a housing comprising:
      an outside container comprising:
         a continuous substantially cylindrical first side wall with an open and substantially circular first top opening and a substantially circular first bottom edge;
         a substantially circular first bottom wall sealed and attached to the first circular bottom edge of the first side wall to form a first sealed receptacle for said heated fluid;
      an inside container comprising:
         a continuous substantially cylindrical second side wall with an open and substantially circular second top opening and a substantially circular and continuous second bottom edge, the second bottom edge sealed to the first circular bottom wall interior to the first bottom edge;
      wherein the inside container is disposed within the outside container, wherein a continuous fluid channel is formed in between the outside container and the inside container and configured to conduct said heated fluid, wherein the channel comprises a circular shape surrounding the inside container, wherein the inside container comprises at least a first slot and at least a second slot each forming a fluid connection between the channel and into the inside container and configured to conduct said heated fluid within the channel and within the inside container, and wherein the inside container is configured and sized to fit a human appendage within;
   (b) a top lid having a top end and a bottom end, wherein the bottom end is formed for fit over and cover the housing and to removably attach to an upper edge of the first side wall of the outside container, and wherein an opening is provided at the top end of the lid leading into the inside container for inserting said human appendage into the inside container;
   (c) a latex wrist seal attached to the top end of the top lid and covering the opening, wherein the latex wrist seal comprises an entrance slot for inserting said human appendage;
   (d) at least one actuated fluid circulator disposed within the housing and operable to rotate the heated fluid in a swirling motion within both the outside container and the inside container, wherein the first slot directs the heated fluid from the channel into the inside container and the second slot directs the heated fluid from the inside container to the channel through the slot, wherein the actuated fluid circulator is an impeller;
   (e) a heating element disposed within the channel and attached to the lid and configured to heat fluid introduced into the housing to continuously provide the heated fluid, wherein the heating element and the at least one motorized impeller are attached to the bottom end of the lid;
   (f) a handle attached to the top end of the top lid and configured to move the lid to cover or uncover the outside and inside containers; and
   (g) a strainer basket suspended within the channel configured to strain therapeutic substances in the heated fluid circulating within the channel or to release the therapeutic substances into the circulating heated fluid.

2. The therapeutic device of claim 1, further comprising a plurality of clips that removably attach the top lid to the housing.

3. The therapeutic device of claim 1, further comprising at least a first partition wall and a second partition wall between the outside container and the inside container forming at least one cavity within the channel.

4. The therapeutic device of claim 3, wherein the cavity is formed to secure at least one of ice, herbs, and a tea bag.

* * * * *